United States Patent
Dala-Krishna

(10) Patent No.: US 8,070,684 B2
(45) Date of Patent: Dec. 6, 2011

(54) METHOD AND SYSTEM FOR EVALUATING VALVULAR FUNCTION

(75) Inventor: Praveen Dala-Krishna, Sicklerville, NJ (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1510 days.

(21) Appl. No.: 11/302,402

(22) Filed: Dec. 14, 2005

(65) Prior Publication Data

US 2007/0167794 A1 Jul. 19, 2007

(51) Int. Cl.
*A61B 8/00* (2006.01)
(52) U.S. Cl. ........ 600/454; 600/437; 600/453; 600/465; 600/479; 600/407; 600/441
(58) Field of Classification Search ............... 600/479, 600/509, 12, 513, 516, 521
See application file for complete search history.

(56) References Cited

U.S. PATENT DOCUMENTS

| | | | |
|---|---|---|---|
| 4,161,121 A | 7/1979 | Zitelli et al. | |
| 4,241,610 A | 12/1980 | Anderson | |
| 4,462,408 A | 7/1984 | Silverstein et al. | |
| 4,519,260 A | 5/1985 | Fu et al. | |
| 4,576,177 A | 3/1986 | Webster, Jr. | |
| 4,605,009 A | 8/1986 | Pourcelot et al. | |
| 4,841,977 A | 6/1989 | Griffith et al. | |
| 4,890,268 A | 12/1989 | Smith et al. | |
| 4,917,097 A | 4/1990 | Proudian et al. | |
| 4,951,677 A | 8/1990 | Crowley et al. | |
| 5,002,059 A | 3/1991 | Crowley et al. | |
| 5,090,956 A | 2/1992 | McCoy | |
| 5,105,819 A | 4/1992 | Wollschlager et al. | |
| 5,152,294 A | 10/1992 | Mochizuki et al. | |
| 5,158,087 A | 10/1992 | Gatzke | |
| 5,170,793 A | 12/1992 | Takano et al. | |
| 5,195,968 A | 3/1993 | Lundquist et al. | |
| 5,254,088 A | 10/1993 | Lundquist et al. | |
| 5,279,559 A | 1/1994 | Barr | |
| 5,307,816 A | 5/1994 | Hashimoto et al. | |
| 5,309,914 A | 5/1994 | Iinuma | |
| 5,325,860 A | 7/1994 | Seward et al. | |

(Continued)

OTHER PUBLICATIONS

Keith S. Dickerson et al., "Comparison of Conventional and Transverse Doppler Sonograms", J. Ultrasound Med., 1993, pp. 497-506, vol. 12.

(Continued)

*Primary Examiner* — Tse Chen
*Assistant Examiner* — Joel F Brutus
(74) *Attorney, Agent, or Firm* — The Marbury Law Group, PLLC

(57) ABSTRACT

A method and apparatus for enhancing evaluation of valvular function in terms of regurgitation is described. The techniques include a method and apparatus for monitoring flow across a valve and evaluating regurgitation through the valve. An ultrasound scanner with Doppler capabilities processes and represents Doppler signal data in a color scale. The Doppler signal data is processed such that different colors are assigned to signals that have different power levels. An ECG signal may be correlated to the Doppler signals to determine systole and diastole periods, then the regurgitation is determined by estimating a peak reverse blood flow based on Doppler signals from blood at systole. The Doppler signals may also be processed so as to determine a cardiac cycle, then regurgitation is determined as the ratio of a reverse blood flow as a percentage of a forward blood flow.

43 Claims, 13 Drawing Sheets

U.S. PATENT DOCUMENTS

| | | | |
|---|---|---|---|
| 5,336,182 A | 8/1994 | Lundquist et al. | |
| 5,345,938 A | 9/1994 | Nishiki et al. | |
| 5,345,940 A | 9/1994 | Seward et al. | |
| 5,357,550 A | 10/1994 | Asahina et al. | |
| 5,358,478 A | 10/1994 | Thompson et al. | |
| 5,364,351 A | 11/1994 | Heinzelman et al. | |
| 5,372,138 A | 12/1994 | Crowley et al. | |
| 5,385,148 A | 1/1995 | Lesh et al. | |
| 5,395,327 A | 3/1995 | Lundquist et al. | |
| 5,409,010 A * | 4/1995 | Beach et al. | 600/455 |
| 5,438,997 A | 8/1995 | Sieben et al. | |
| 5,456,258 A | 10/1995 | Kondo et al. | |
| 5,456,664 A | 10/1995 | Heinzelman et al. | |
| 5,470,350 A | 11/1995 | Buchholtz et al. | |
| 5,477,858 A * | 12/1995 | Norris et al. | 600/441 |
| 5,499,630 A | 3/1996 | Hiki et al. | |
| 5,515,853 A | 5/1996 | Smith et al. | |
| 5,515,856 A | 5/1996 | Olstad et al. | |
| 5,531,686 A | 7/1996 | Lundquist et al. | |
| 5,560,362 A | 10/1996 | Sliwa, Jr. et al. | |
| 5,588,432 A | 12/1996 | Crowley | |
| 5,622,174 A | 4/1997 | Yamazaki | |
| 5,662,116 A | 9/1997 | Kondo et al. | |
| 5,697,965 A | 12/1997 | Griffin, III | |
| 5,699,805 A | 12/1997 | Seward et al. | |
| 5,701,897 A | 12/1997 | Sano | |
| 5,704,361 A | 1/1998 | Seward et al. | |
| 5,713,363 A | 2/1998 | Seward et al. | |
| 5,715,817 A | 2/1998 | Stevens-Wright et al. | |
| 5,722,403 A | 3/1998 | McGee et al. | |
| 5,749,364 A | 5/1998 | Sliwa, Jr. et al. | |
| 5,788,636 A | 8/1998 | Curley | |
| 5,795,299 A | 8/1998 | Eaton et al. | |
| 5,797,848 A | 8/1998 | Marian et al. | |
| 5,800,356 A | 9/1998 | Criton et al. | |
| 5,807,324 A | 9/1998 | Griffin, III | |
| 5,846,205 A | 12/1998 | Curley et al. | |
| 5,888,577 A | 3/1999 | Griffin, III et al. | |
| 5,891,088 A | 4/1999 | Thompson et al. | |
| 5,906,579 A | 5/1999 | Vander Salm et al. | |
| 5,916,168 A | 6/1999 | Pedersen et al. | |
| 5,921,978 A | 7/1999 | Thompson et al. | |
| 5,928,276 A | 7/1999 | Griffin, III et al. | |
| 5,931,863 A | 8/1999 | Griffin, III et al. | |
| 5,935,102 A | 8/1999 | Bowden et al. | |
| 5,938,616 A | 8/1999 | Eaton et al. | |
| 5,954,654 A | 9/1999 | Eaton et al. | |
| 6,013,072 A | 1/2000 | Winston et al. | |
| 6,033,378 A | 3/2000 | Lundquist et al. | |
| 6,039,693 A | 3/2000 | Seward et al. | |
| 6,085,117 A | 7/2000 | Griffin, III et al. | |
| 6,144,870 A | 11/2000 | Griffin, III | |
| 6,171,248 B1 | 1/2001 | Hossack et al. | |
| 6,173,205 B1 | 1/2001 | Griffin, III et al. | |
| 6,190,353 B1 | 2/2001 | Makower et al. | |
| 6,210,333 B1 | 4/2001 | Gardner et al. | |
| 6,224,556 B1 | 5/2001 | Schwartz et al. | |
| 6,228,028 B1 | 5/2001 | Klein et al. | |
| 6,228,032 B1 | 5/2001 | Eaton et al. | |
| 6,261,246 B1 | 7/2001 | Pantages et al. | |
| 6,293,943 B1 | 9/2001 | Pansecu et al. | |
| 6,306,096 B1 | 10/2001 | Seward et al. | |
| 6,306,097 B1 | 10/2001 | Park et al. | |
| 6,310,828 B1 | 10/2001 | Mumm et al. | |
| 6,358,208 B1 | 3/2002 | Long et al. | |
| 6,360,027 B1 | 3/2002 | Hossack et al. | |
| 6,368,275 B1 | 4/2002 | Sliwa et al. | |
| 6,385,489 B1 | 5/2002 | Griffin, III et al. | |
| 6,398,731 B1 | 6/2002 | Mumm et al. | |
| 6,423,002 B1 | 7/2002 | Hossack | |
| 6,440,488 B2 | 8/2002 | Griffin, III et al. | |
| 6,443,894 B1 | 9/2002 | Sumanaweera et al. | |
| 6,475,148 B1 | 11/2002 | Jackson et al. | |
| 6,475,149 B1 | 11/2002 | Sumanaweera | |
| 6,482,161 B1 | 11/2002 | Sumanaweera et al. | |
| 6,485,455 B1 | 11/2002 | Thompson et al. | |
| 6,491,633 B1 | 12/2002 | Krishnan et al. | |
| 6,503,202 B1 | 1/2003 | Hossack et al. | |
| 6,517,488 B1 | 2/2003 | Hossack | |
| 6,527,717 B1 | 3/2003 | Jackson et al. | |
| 6,532,378 B2 | 3/2003 | Saksena et al. | |
| 6,544,181 B1 * | 4/2003 | Buck et al. | 600/455 |
| 6,554,770 B1 | 4/2003 | Sumanaweera et al. | |
| 6,589,182 B1 | 7/2003 | Loftman et al. | |
| 6,605,043 B1 | 8/2003 | Dreschel et al. | |
| 6,607,488 B1 | 8/2003 | Jackson et al. | |
| 6,607,528 B1 | 8/2003 | Quick et al. | |
| 6,612,992 B1 | 9/2003 | Hossack et al. | |
| 6,645,147 B1 | 11/2003 | Jackson et al. | |
| 6,648,875 B2 | 11/2003 | Simpson et al. | |
| 6,709,396 B2 | 3/2004 | Flesch et al. | |
| 6,908,434 B1 | 6/2005 | Jenkins et al. | |
| 6,923,768 B2 | 8/2005 | Camus et al. | |
| 2003/0045796 A1 | 3/2003 | Friedman | |
| 2003/0109785 A1 * | 6/2003 | Buck et al. | 600/437 |
| 2003/0158483 A1 | 8/2003 | Jackson et al. | |
| 2004/0097805 A1 | 5/2004 | Verard et al. | |
| 2004/0127798 A1 * | 7/2004 | Dala-Krishna et al. | 600/450 |
| 2004/0249282 A1 | 12/2004 | Olstad | |
| 2004/0254483 A1 * | 12/2004 | Zdeblick et al. | 600/486 |
| 2005/0203390 A1 | 9/2005 | Torp et al. | |

OTHER PUBLICATIONS

David J. Sahn, "Phased Arrays for Multiplane Esophageal Echos in Infants", Summary Statement, Diagnostic Radiology Study Section, Jun. 1990.

David J. Sahn, "Instrumentation and Physical Factors Related to Visualization of Stenotic and Regurgitant Jets by Doppler Color Flow Mapping", JACC, Nov. 1988, pp. 1354-1365, vol. 12, No. 5.

David J. Sahn, "Advances in Ultrasound Imaging for Congenital Heart Disease Diagnosis and Management", Pediatric Cardiology, Nov. 26-Dec. 1, 1989, Proceedings of the III World Congress of Pediatric Cardiology, Bangkok.

David J. Sahn et al., "Important Roles of Transeophageal Color Doppler Flow Mapping Studies(TEE) in Infants with Congenital Heart Disease", Supplement to Journal of the American College of Cardiology, Feb. 1990, vol. 15, No. 2 (Supplement A).

David J. Sahn, "Applications of Color Flow Mapping in Pediatric Cardiology", Cardiology Clinics, May 1989, pp. 255-264, vol. 7, No. 2.

David J. Sahn et al., "Miniaturized High Frequency Phased Array Devices for High Resolution Neonatal and Intraoperative Imaging", Supplement to Journal of the American College of Cardiology, Feb. 1990, vol. 15, No. 2 (Supplement A).

Piero Tortoli et al., "Velocity Magnitude Estimation with Linear Arrays Using Doppler Bandwidth", Ultrasounics, 2001, pp. 157-161, vol. 39.

Lilliam M. Valdes-Cruz et al., "Transvascular Intracardiac Applications of a Miniaturized Phase-Array Ultrasonic Endoscope", Brief Rapid Communication, Mar. 1991, pp. 1023-1027, vol. 83, No. 3.

Lilliam M. Valdes-Cruz et al., "Experimental Animal Investigations of the Potential for New Approaches to Diagnostic Cardiac Imaging in Infants and Small Premature Infants from Intracardiac and Trasesophageal Approaches Using a 20MHz Real Time Ultrasound Imaging Catheter", Supplement to Journal of the American College of Cardiology, Feb. 1989, vol. 13, No. 2 (Supplement A).

P.N.T. Wells, "Velocity, Absorption and Attenuation in Biological Materials", Biomedical Ultrasonics, 1977, pp. 110-144.

Antonio L. Bartorelli, M.D. et al., "Plaque Characterization of Atherosclerotic Coronary Arteries by Intravascular Ultrasound", Echocardiography: A Journal of CV Ultrasound & Allied Tech, 1990, pp. 389-395, vol. 7, No. 4.

N. Bom et al., "Early and recent intraluminal ultrasound devices", International Journal of Cardiac Imaging, 1989, pp. 79-88, vol. 4.

R.J. Crowley et al., "Optimized ultrasound imaging catheters for use in the vascular system", International Journal of Cardiac Imaging, 1989, pp. 145-151, vol. 4.

R.J. Crowley, et al., "Ultrasound guided therapeutic catheters: recent developments and clinical results", International Journal of Cardiac Imaging, 1991, pp. 145-156, vol. 6.

Richard A. Carleton, M.D., et al., "Measurement of Left Ventricular Diameter in the Dog by Cardiac Catheterization", Circulation Research, May 1968, pp. 545-558, vol. XXII.

Taher Elkadi et al., "Importance of Color Flow Doppler (CFD) Imaging of the Right Ventricular Outflow Tract and Pulmonary Arteries by Transesophageal Echocardiography (TEE) During Surgery for CHD", Supplement III Circulation, Oct. 1990, p. III-438, vol. 82, No. 4.

Philip C. Currie, "Transeosphageal Echocardiography New Window to the Hearth", Circulation, Jul. 1989, pp. 215-217, vol. 88, No. 1.

Steven Schwartz et al., "In Vivo Intracardiac 2-D Echocardiography: Effects of Transducer Frequency, Imaging Approached and Comparison with Fiberoptic Angioscopy", JACC, Feb. 1990, pp. 29A, vol. 15, No. 2.

J. Souquet et al., "Transesophageal Phased Array for Imaging the Heart", IEEE Transactions on Biomedical Engineering, Oct. 1982, pp. 707-712, vol. BME-29, No. 10.

Craig J. Hartley, "Review of Intracoronary Doppler catheters", International Journal of Cardiac Imaging, 1989, pp. 159-168, vol. 4.

John McB. Hodgson et al., "Percutaneous Intravascular Ultrasound Imaging: Validation of a Real-Time Synthetic Aperture Array Catheter", American Journal of Cardiac Imaging, Mar. 1991, pp. 56-71, vol. 5, No. 1.

J. McB. Hodgson et al., "Clinical percutaneous imaging of corronary anatomy using an over-the-wire ultrasound catheter system", International Journal of Cardiact Imaging, 1989, pp. 187-193, vol. 4.

Brenda S. Kusay et al., "Realtime in Vivo Intracardiac Two-Dimensional Echocardiography and Color Flow Imaging: Approaches, Imaging Planes, and Echo Anatomy", Abstracts of the 62$^{nd}$ Scientific Sessions, 1989, p. II-581.

Charles T. Lancee, "A Transesophageal Phased Array Transducer for Ultrasonic Imaging of the Heart", 1987.

Natesa Pandian et al., "Enhanced Depth of Field in Intracardiac 2-D Echocardiography with a New Prototype, Low Frequency (12 MHz, 9 French) Ultrasound Catheter", Supplemental III Circulation, Oct. 1990, p. III-442, vol. 82, No. 4.

Natesa G. Pandian, M.D. et al., "Intravascular and Intracardiac Ultrasound Imaging: Current Research and Future Directions", Echocardiography: A Journal of CV Ultrasound & Allied Tech., 1990, pp. 377-387, vol. 7, No. 4.

Natesa G. Pandian, M.D. et al., "Intracardiac, Intravascular, Two-Dimensional, High-Frequency Ultrasound Imaging of Pulmonary Artery and Its Branches in Humans and Animals", Circulation, Jun. 1990, pp. 2007-2012, vol. 81, No. 6.

F. Ricou et al., "Applications of intravascular scanning and transesophageal echocardiography in congenital heart disease: tradeoffs and the merging of technologies", International Journal of Cardiac Imaging, 1991, pp. 221-230, vol. 6.

Samuel B. Ritter, M.D., et al., "Transesophageal real time Doppler flow imaging in congenital heart disease: experience with a new pediatric trasducer probe", 1989, Dynamedia, Inc.

Samuel B. Ritter, M.D., et al., "Pediatric Transesophageal Color Flow Imaging: Smaller Probes for Smaller Hearts", 1989.

David J. Sahn, M.D., et al., "Important Roles of Transesophageal Color Doppler Flow Mapping Studies (TEE) in Infants With Congenital Heart Disease", IACC, Feb. 1990, p. 204A, vol. 15, No. 2.

David J. Sahn, M.D. et al., "Miniaturized High Frequency Phased Array Devices for High Resolution Neonatal and Intraoperative Imaging", JACC, Feb. 1990, p. 10A, vol. 15, No. 2.

David J. Sahn, M.D., et al., "Phased Arrays for Multiplane Esophageal Echos in Infants", Grant Application, Department of Health and Human Services Public Health Service, 1992.

Steven Schwartz, M.D., et al., "Intracardiac Echocardioraphic Guidance and Monitoring During Aortic and Mitral Balloon Valvuloplasty", JACC, Feb. 1990, p. 104A, vol. 15, No. 2.

James B. Seward, M.D. et al., "Biplanar Transesophageal Echocardiography: Anatomic Correlations, Image Orientation, and Clinical Applications", Mayo Clin Proc., 1990, pp. 1198-1213, vol. 65.

James B. Seward, M.D. et al., "Wide-Field Transesophageal Echocardiographic Tomography: Feasibility Study", Mayo Clin Proc. 1990, pp. 31-37, vol. 65.

Khalid H. Sheikh, M.D., et al., "Interventional Applications of Intravascular Ultrasound Imaging: Initial Experience and Future Perspectives", Echocadiography: A Journal of CV Ultrasound & Allied Tech., pp. 433-441, vol. 7, No. 4.

Paul G. Yock, M.D., et al., "Two-Dimensional Intravascular Ultrasound: Technical Development and Initial Clinical Experience", Journal of American Society of Echocardiography, 1989, pp. 296-304, vol. 2, No. 4.

Paul G. Yock, M.D. et al., "Real-Time, Two-Dimensional Catheter Ultrasound: A New Technique for High-Resolution Intravascular Imaging", JACC, Feb. 1988, p. 130A, vol. 11, No. 2.

P. Yock et al., "Intravascular Two-Dimensional Catheter Ultrasound: Initial Clinical Studies", Abstracts of the 61$^{st}$ Scientist Sessions, p. II-21.

Michael J. Eberle et al., "Validation of a New Real Time Percotaneous Intravascular Ultrasound Imaging Catheter", Abstracts of the 61$^{st}$ Scientist Sessions, p. II-21.

Natasa Pandian et al., "Intralurolonal Ultrasound Angloscopic Detection of Arterial Dissection and Intimal Flaps: In Vitro and In Vivo Studies", Abstracts of the 61$^{st}$ Scientist Sessions, p. II-21.

John A. Mallery et al., "Evaluation of an Intravascular ultrasound Imaging Catheter in Porcine Peripheral and Coronary Arteries In Vivo", Abstracts of the 61$^{st}$ Scientist Sessions, p. II-21.

Andrew Wintraub, M.D., "Realtime Intracardiac Two-Dimensional Echocardiography in the Catheterization Laboratory in Humans", Intravascular Imaging I, Mar. 19, 1990.

* cited by examiner

METHOD AND SYSTEM FOR EVALUATING VALVULAR FUNCTION

BACKGROUND

1. Field

The present invention relates generally to medical imaging systems, and more particularly to a method and apparatus for evaluating regurgitation of blood from heart valves.

2. Background

Regurgitation, or the backward flow of blood through a defective heart valve, is a critical measurement used quite extensively in cardiology. Ideally, all the blood that is passed from one chamber of the heart to another chamber gets pumped out by the second chamber. Valves in the heart should prevent the flow of blood from a succeeding chamber back to a preceding chamber. For example, a mitral valve between the left atrium chamber of the heart stops flow back into the left ventricle chamber of the heart. However, in some diseased hearts, the valves operation might not be optimal. In such cases some amount of regurgitation, or back-flow, exists from a higher pressure succeeding chamber to a lower pressure preceding chamber.

Ultrasound devices have been developed and refined for the diagnosis and treatment of various medical conditions. Such devises have been developed, for example, to track the magnitude and direction of moving objects, or the position of moving objects over time. By way of example, Doppler echocardiography is one ultrasound technique that is used to determine information about the motion of blood and tissue for the diagnosis and treatment of cardiac conditions. In echocardiography the motion information is obtained from recordings and measurements of Doppler data.

The Doppler principle, as used in Doppler echocardiography, is well known and generally involves exploiting an observed phenomenon that the frequency of reflected ultrasound pulses is altered by a moving object, such as moving tissue or blood cells. This alteration, or change, in frequency is generally referred to as a Doppler shift, with the magnitude of the frequency change, or Doppler shift, being related to the velocity of the moving object form which the ultrasound pulses are reflected. The polarity of the frequency change, or Doppler shift, is related to the direction of motion relative to the ultrasound source: a positive frequency shift (increase) indicates the motion is towards the ultrasound sensor and a negative frequency shift (decrease) indicates that the motion is away from the ultrasound sensor. As such, the magnitude and polarity of the Doppler shift can be used to track the magnitude and direction of moving objects.

Intra-cardiac ultrasonic imaging, a technique where a steerable catheter fitted with an ultrasound transducer on its tip is used to view the interior anatomy of a beating heart has significantly improved the definition and clarity of views of diseased valves. However, a drawback to intra-cardiac ultrasound imaging is the need to account for a field of view which is constantly in motion. Furthermore, given the dynamics of an interventional cardiology procedure, where intra-cardiac ultrasound is predominantly employed, an imaging catheter could also be in constant motion due to blood flow. This can cause measurements difficulties, due to the dynamic qualities involved, such as the dynamics of the field of view and the catheter. In addition, the position of the ultrasound imaging head, or transducer, can be restricted to fields of view where the blood flow across a valve being studied is close to orthogonal to the ultrasound beam, where existing Doppler techniques have difficulty operating. It is also desirable, in many cases, to assign a quantitative value, or number, to regurgitation measurements and associated abnormal flow patterns, including turbulence.

Thus, a need exists for improved measurement and quantification of heart valve regurgitation.

SUMMARY

Embodiments disclosed herein address the above stated needs by providing methods and apparatus for improving measurement and quantification of regurgitation. The techniques monitor flow across a valve and evaluate regurgitation through the valve. Monitoring the flow may be performed either semi-automatically or automatically. Techniques to assess the flow even in the case where the flow across the valve is orthogonal to the imaging-line from the transducer are also disclosed. The techniques can be used with Doppler data collected using an ultrasound transducer attached to a steerable catheter used to view the interior anatomy of a heart to perform intra-cardiac ultrasonic imaging.

In one embodiment an ultrasound scanner with Doppler capabilities processes and represents Doppler signal data in a color scale. The color scale can be determined in many different ways, for example through a functionality similar to a "look-up table." The Doppler signal data is processed such that different colors are assigned to the signal based on its power level. For example, different power levels in the processed signal may be represented in two or more colors. The color scale may be either dynamically generated or previously set up in the system through any combination of hardware or software.

An ultrasound scanner system may also capture and display an electrocardiogram (ECG) of a patient as well. In such a system, signals from blood, which can be identified by their received power levels and corresponding color, may be tracked. Depending upon the angle between the blood flow and the ultrasound beam, blood flow in the reverse direction (regurgitation) may be determined, or estimated, for example, by utilizing correlation with the ECG to determine phases of the cardiac cycle. Tracking techniques may be applied to locate peak flows in either direction and the total flow in either direction may be determined, or estimated, per cardiac cycle to provide a numerical estimate of regurgitation. In cases where the blood flow is orthogonal to the line of interrogation of the ultrasound, the overall bandwidth of the resulting Doppler signal is ascertained, again using the power levels to differentiate between tissue and blood, and the peak bandwidth at various points along the cardiac cycle are estimated and thus an estimation of regurgitation is obtained. Alternatively, in another embodiment, such bandwidth based estimates can also be used to judge overall turbulence in flow, such as flow in the atrial appendage etc. In another embodiment, a user can indicate, either on the ECG or on the Doppler spectrum, an area of interest where reverse flow through the valve is to be determined or estimated.

In yet another embodiment, a user may outline an area in a Color Doppler image pertaining to flow around a valve. In such a case, the base-line adjusted color Doppler representation of flow through a valve is captured as a color image. The relative width of the reverse flow, which can be denoted by a different color to that of normal flow through the valve, may then be measured as an area and translated to volumetric flow assuming a conical volume extrapolation or such other area to volume extrapolated fit. The translation may be performed automatically.

Other features and advantages of the present invention should be apparent from the following description of exemplary embodiments, which illustrate, by way of example, aspects of the invention.

DETAILED DESCRIPTION

The word "exemplary" is used herein to mean "serving as an example, instance, or illustration." Any embodiment described herein as "exemplary" is not necessarily to be construed as preferred or advantageous over other embodiments.

Some difficulties can be presented by intra-cardiac ultrasonic imaging, including the need to account for a field of view which is constantly in motion. The imaging catheter could be in constant motion due to blood flow, and the position of the ultrasound imaging head, or transducer, can be restricted to fields of view where the blood flow across a valve being studied is close to orthogonal to the ultrasound beam. Some of the issues raised by a field of view that is constantly in motion, along with limitations of operator interaction in a practical interventional cardiology application, are addressed in co-pending U.S. patent application Ser. No. 11/302,391, entitled METHOD AND SYSTEM FOR ENHANCING SPECTRAL DOPPLER PRESENTATION, filed Dec. 14, 2005, assigned to the assignee of the present application and hereby incorporated herein in its entirety.

In co-pending U.S. patent application Ser. No. 11/302,391, techniques are described for displaying Doppler spectral data, wherein Doppler signals from any strong reflectors, such as tissue, within the sample volume are shown in a different color than signals from weaker reflectors, such as blood. Such a differentiation is obtained by displaying frequency components with different amplitudes, or power levels, in different colors.

Techniques are described below to improve the measurement and quantification of regurgitation. Techniques of monitoring flow across a valve and evaluating regurgitation through the valve either semi-automatically or automatically are described. Techniques to assess flow across a valve and evaluate regurgitation, even in the case where the flow across the valve is orthogonal to the imaging-line from the transducer, are also described. The techniques described include both semi-automated, and fully-automated estimation of regurgitation. Also, estimating regurgitation can be done real-time, when the data is being acquired, or off-line, that is, storing ultrasound data and processing it later.

Figure 1:
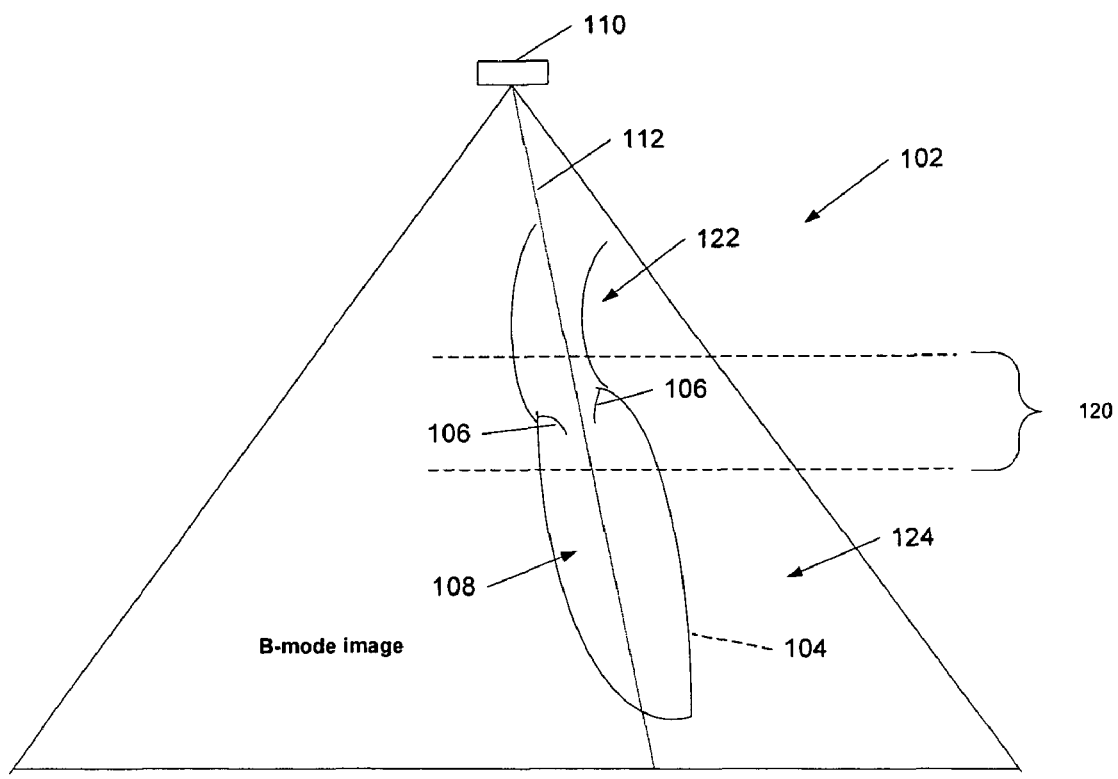
FIG. 1 is an illustration of an ultrasound sector.

FIG. 1 is an illustration of an ultrasound sector 102. In this example, the ultrasound is being used to examine portions of a heart valve. The heart valve 104 includes leaflets 106 with blood 108 flowing through the valve 104 and valve leaflets 106.

As shown in FIG. 1, an ultrasound transceiver 110, includes an ultrasound transmitter and an ultrasound receiver, transmits an ultrasound beam 112, or a plurality of beams. For example, a single ultrasound beam can form the entire sector at once, or a narrow beam may be swept through an arc forming the sector, or multiple beams may be transmitted simultaneously to form the sector, or other techniques as is known to those of skill in the art. For purposes of illustration a single instance of an ultrasound beam 112 is illustrated within the sector 102. As the ultrasound beam 112 propagates through the sector it interacts with the material within its path that includes the heart valve 104, heart valve leaflets 106 and blood 108.

In this example the ultrasound is "range gated" so that only the region of interest 120 around the heart valve leaflets 106, and the surrounding blood 108, are examined. Thus, the region of the sector 102 that the ultrasound beam 112 passes through before and after the area of interest, 122 and 124 respectively, are not examined and not displayed in the Doppler presentation.

Doppler signals may be obtained from the area of interest 122 that includes a valve being evaluated wherein a relevant majority of the cross-section of the valve is included within the area of interest 120. As described in co-pending U.S. patent application Ser. No. 11/302,391, the signals may be processed to distinguish signals received from blood from those received from tissue, and then different colors may be assigned to the different signals. The signals can then be processed in different ways to obtain regurgitation. For example, the processed Doppler signals can be correlated to an ECG signal to determine systole and diastole of the heart. The peak reverse flow at systole, such as in the case with interrogation of the atrio-ventricular valves, may then be measured. In another example, peak forward and reverse flow may be measured during a given cardiac cycle, where the cardiac cycle is identified by a periodic repetition of a peak value, or a pattern of flow, or a positive to negative flow translation in a given direction. Regurgitation may then be estimated using the ratio of reverse flow as a percentage of forward flow. The forward and reverse flows are given by the area under the respective forward flow and reverse flow curves, normalized for the angle between the ultrasound beam and the blood flow.

Figure 2:
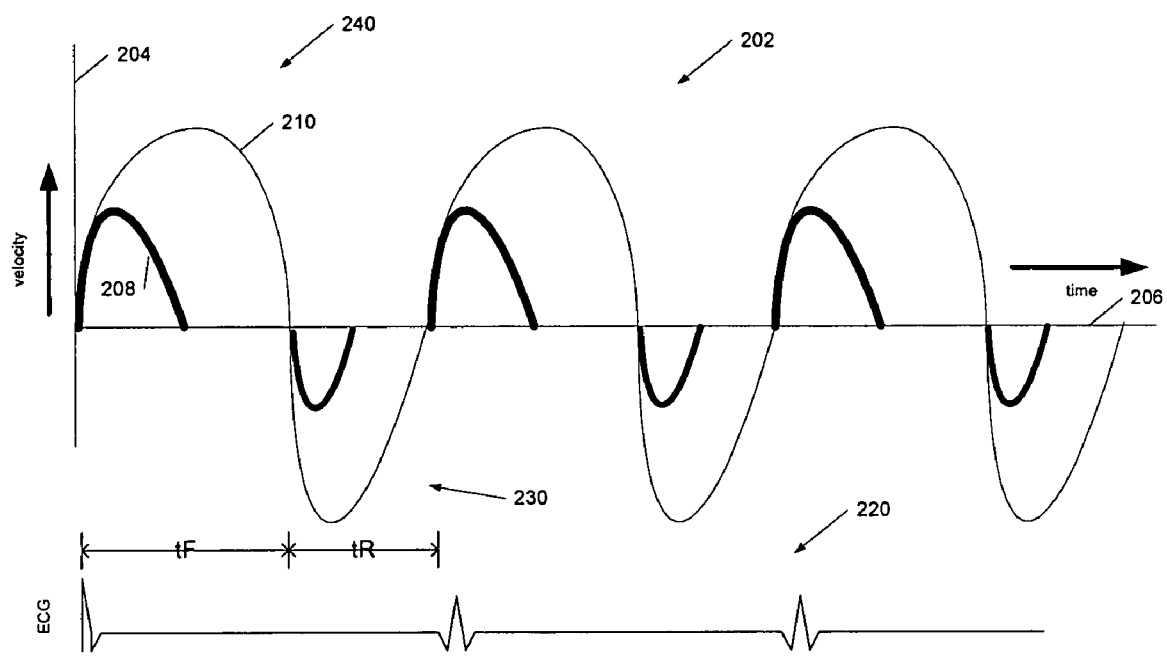
FIG. 2 is a display illustrating a Doppler signal that would be received from the individual components of the heart valve and blood.

FIG. 2 is a display illustrating a Doppler signal 202 that would be received from the individual components of the heart valve and blood. As shown in FIG. 2, the display has a vertical axis 204 that represents velocity as measured by the Doppler shift of the ultrasound beam as it passes through the area of interest that includes the heart value leaflets and surrounding blood. The horizontal axis 206 represents time. In FIG. 2 the Doppler signal 202 includes Doppler information from both the heart tissue, primarily the heart leaflets, 208 and the blood 210 flowing through the leaflet.

Also included in FIG. 2 is an ECG trace 220. As noted, the Doppler signals can be correlated to an ECG signal to determine systole and diastole of the heart. The peak reverse flow at systole, such as in the case with interrogation of the atrio-ventricular valves, may then be measured.

It is noted that the spectral Doppler information can be obtained from the ultrasonic interrogation device either as a spectrum, that is digitized line data as a function of time, or digitized images, or the Doppler information may be obtained as an audio signal output which is subsequently digitized and processed to obtain a velocity-time profile Doppler display 202.

In cases where color Doppler is the mode of interrogation, various frames, or a sampling of frames, that form a real time image may be analyzed as a function of the ECG 220, with the ECG being utilized to denote the phases of the cardiac cycle. In such an application, the presence or absence of a particular color, and hence directional flow, as indicated by the Doppler display 202 during a particular phase of the cardiac cycle, can be detected. Also, the number of pixels in the Doppler display that are assigned a particular color and the duration of persistence of that color through the cardiac cycle provides additional information regarding regurgitation.

For example, consider the case where the valve is being imaged from the atrium, with backflow from the valve being directed straight at the transducer, and the color code for blood flow towards the transducer is graduated in a color scale from red to yellow for increasing velocity up to, for example, 0.8 m/sec. At systole, the display portion 230 showing regurgitation appears as a red/yellow colored flow emanating out of the atrio-ventricular valve in question. By compensating for angle between the ultrasound beam and the blood flow, the color scale can be recalibrated to more accurately depict the velocity. Knowledge of the imaging frame rate, or sub-sampling rate if a framegrabber or other video capture device is employed to obtain these images, and knowledge of the cardiac cycle (start of systole), can be used to determine the velocity profile of peak flow velocity through the valve as a function of time. The end of this cycle may be considered either as a function of the ECG, or when flow towards the transducer has stopped. Similarly, flow away from the transducer 240 can be analyzed to provide a time-velocity profile. Regurgitation can be calculated from the time-velocity profile as described in the case of spectral-Doppler.

Figure 3:
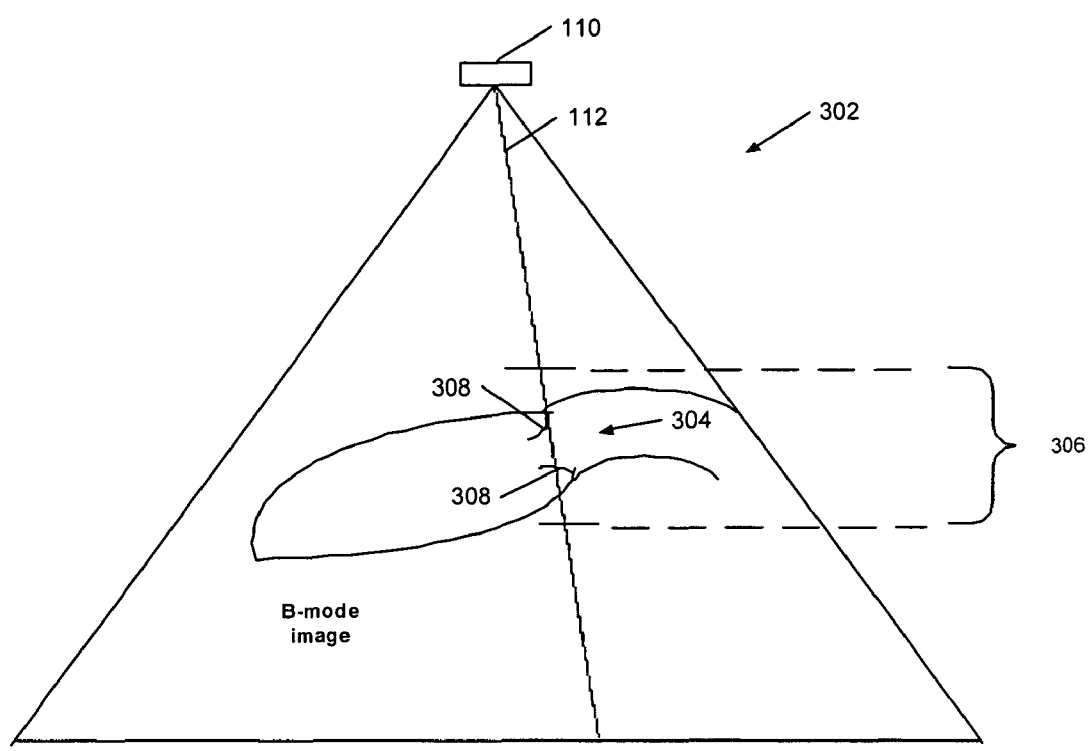
FIG. 3 is a block diagram illustrating another ultrasound sector.

FIG. 3 is a block diagram illustrating an ultrasound sector 302. In this example, an ultrasound transceiver 110, that includes an ultrasound transmitter and an ultrasound receiver, transmits an ultrasound beam 112, or a plurality of beams, that are orthogonal to the direction of blood flow 304. In this example, range gating techniques are used so that a region of interest 306 around the heart value leaflets 308, and the surrounding blood 304, are examined.

Figure 4:
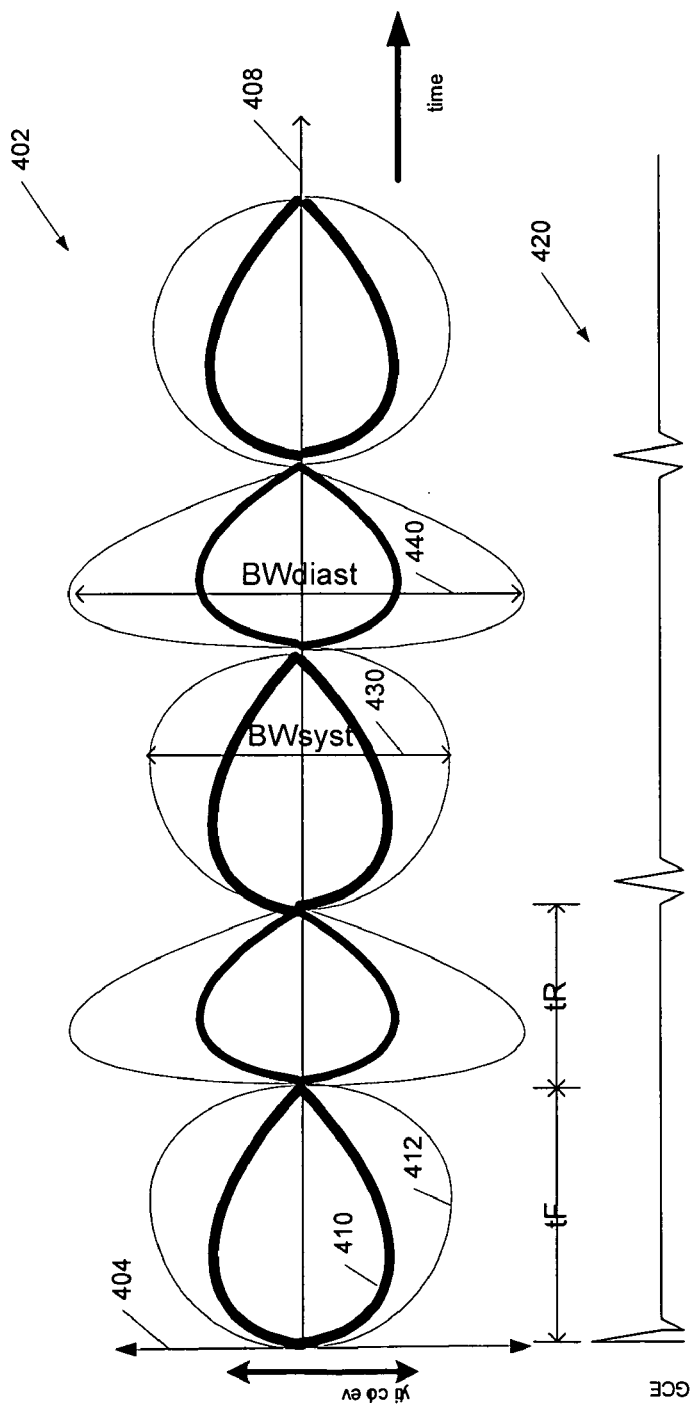
FIG. 4 is a Doppler signal display representing the Doppler signal that would be received from the individual components of the heart valve and blood.

FIG. 4 is a Doppler signal display 402 representing the Doppler signal that would be received from the individual components of the heart valve and blood. As shown in FIG. 4, the display has a vertical axis 404 that represents velocity as measured by the Doppler bandwidth of backscattered signals. The horizontal axis 408 represents time. In FIG. 4 the Doppler display 402 includes Doppler information from both the heart tissue, primarily the heart leaflets 410, and the blood 412 flowing through the leaflet. Techniques for estimating velocity based on Doppler bandwidths are known to those of skill in the art. See Tortoli P, Guidi G, Mantovani L, Newhouse V L, "Velocity magnitude estimation with linear arrays using Doppler bandwidth." Ultrasonics. 2001 April; 39(3):157-61, and Dickerson K S, Newhouse V L, Tortoli P, Guidi G, "Comparison of conventional and transverse Doppler sonograms" J Ultrasound Med. 1993 September; 12(9):497-506, incorporated by reference herein in their entirety.

In conditions when the blood flow is nearly perpendicular to the interrogating ultrasound beam, as illustrated in FIGS. 3 and 4, the overall Doppler bandwidth of the spectrum may be determined as a function of systole bandwidth 430 and diastole bandwidth 440. A time-bandwidth profile may then be determined. Regurgitation can be estimated using the ratio of the flow velocity and time product.

Figure 5:
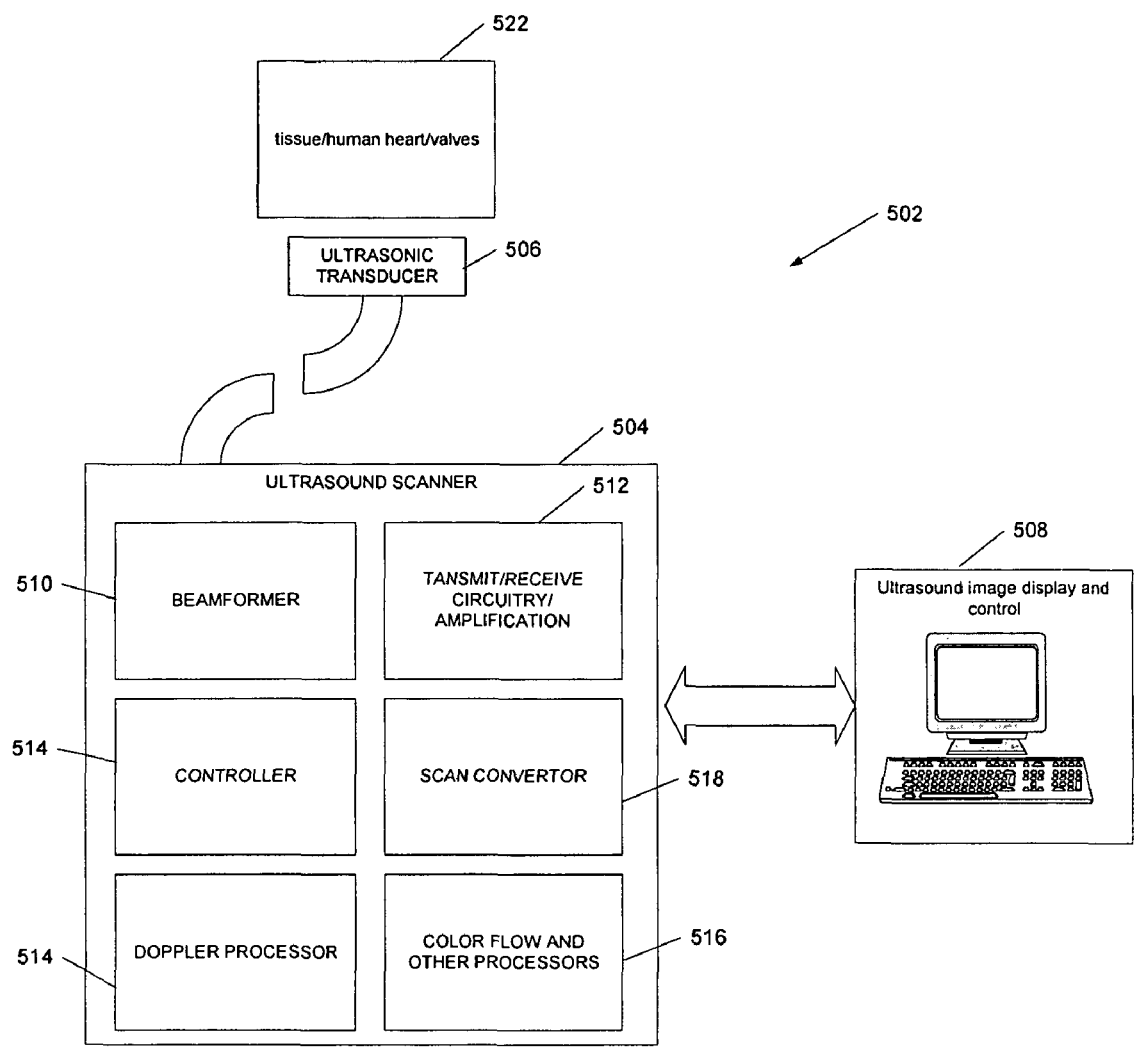
FIG. 5 is a block diagram illustrating an embodiment of a Doppler scanner system.

The techniques described can be implemented in many different systems. FIG. 5 is a block diagram illustrating an embodiment of a Doppler scanner system 502 constructed in accordance with the present invention. The system 502 includes an ultrasound scanner 504, an ultrasonic transducer 506, and a display 508. The ultrasound scanner 504 can be capable of intercepting and interpreting Doppler signals. The ultrasound scanner 504 may include various circuits and subsystems for performing various functions. For example, the ultrasound scanner 506 can include beamformer 510 and transmit/receive 512 circuits or subsystems. The ultrasound scanner 504 may also include a Doppler processor 514, and color flow and other processor 516. The Doppler processor 514 can process spectral Doppler signals as well as process Doppler bandwidth. The ultrasound scanner 504 may also include a scan converter 518 and a controller 520.

The ultrasound scanner 504 generates signals that are communicated to the ultrasonic transducer 506. The ultrasonic transducer transmits signals and receives reflected signals from a desired sample 522, for example from a human heart tissue and blood. Signals received by the ultrasonic transducer 506 are communicated to the ultrasound scanner 504. In one embodiment, the ultrasound scanner 504 processes the received signals, including color mapping, and the processed signal is provided to the display 508 for presentation to a user. In another embodiment, the ultrasound scanner 504 processes the received signal and the display 508 includes a processor that processes the signal, for example to perform color mapping, before presentation to a user. Determining regurgitation can be performed in the ultrasound scanner 504, a processor associated with the display 508, or both.

In general, the ultrasound scanner 504 includes a combination of digital or analog electronics capable of generating necessary signals and processing such received signals so as to generate Doppler representations and determine regurgitation in accordance with the invention. In addition, processing of the Doppler signals and determining regurgitation may be performed in real-time, that is at the time the signals are captured, or off-line following the capture of the data.

The ultrasonic transducer 506 can include, for example, one or more transducers that utilize piezoelectric properties to generate acoustic signals from electrical signals. The transducer may be a mechanical, sector, linear, or curved array design. In general, the type of transducer used is selected to be appropriate for the particular application such as an external application, trans-oesophageal, intra-vascular, intra-cardiac, or endocavitary applications.

Figure 6:
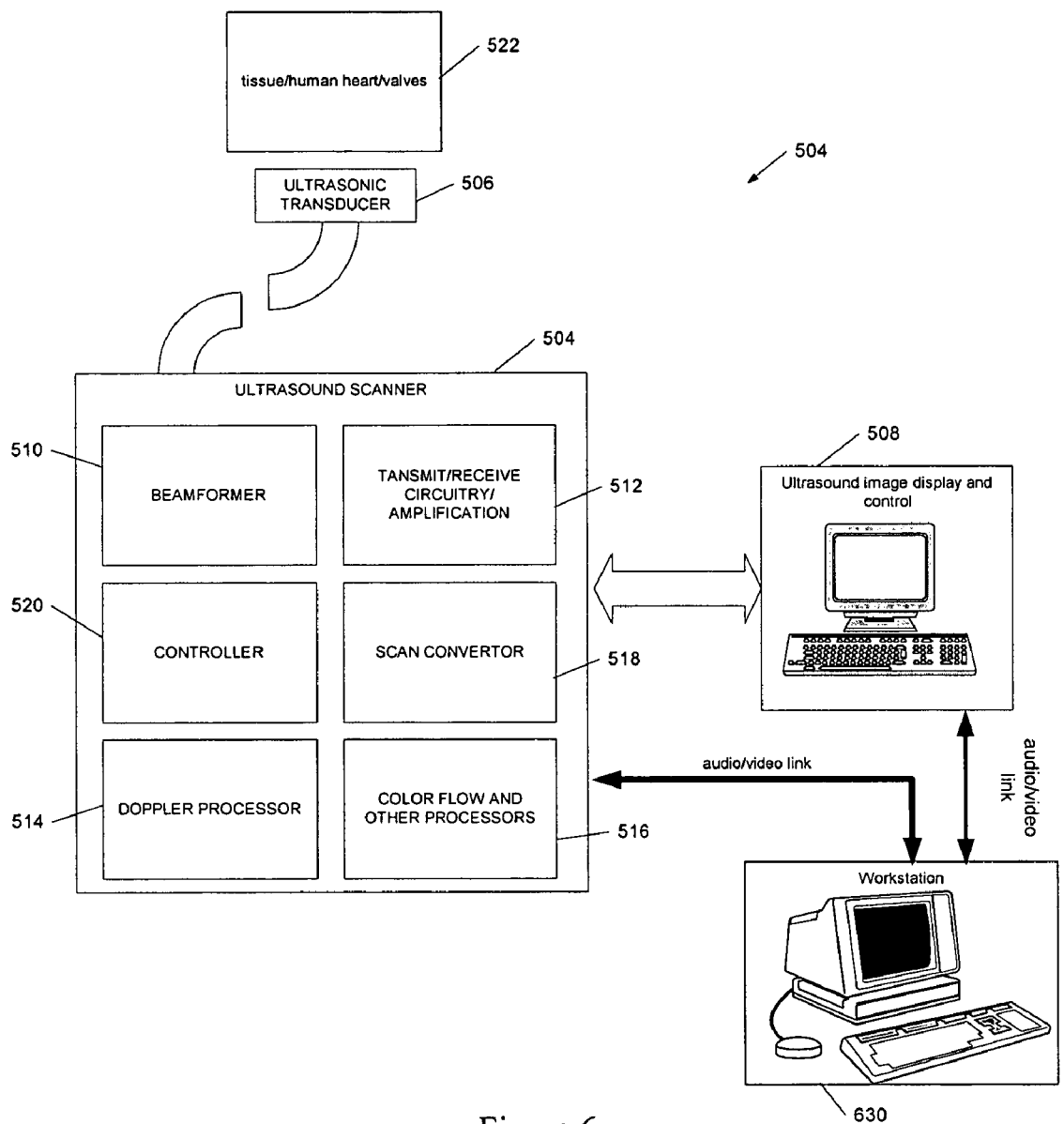
FIG. 6 is a block diagram of the Doppler scanner system of FIG. 5 and includes a workstation.

FIG. 6 is a block diagram of the Doppler scanner system of FIG. 5 and includes a workstation 630. In the embodiment of FIG. 6, the workstation 630 may include hardware and/or software that is separate from the ultrasound scanner 504. The workstation 630 may be in communication with the ultrasound scanner 504, the display 508, or both. For example, video, audio, or both may be communicated between the ultrasound scanner 504 and the display 508. Communication between the workstation 530, the display 506 and the ultrasound scanner 504 can include video, audio, Electrocardiogram (ECG) signals, or other types of signals in either digital and/or analog format. The above described techniques can then be performed either partially or entirely on the workstation 530

Figure 7:
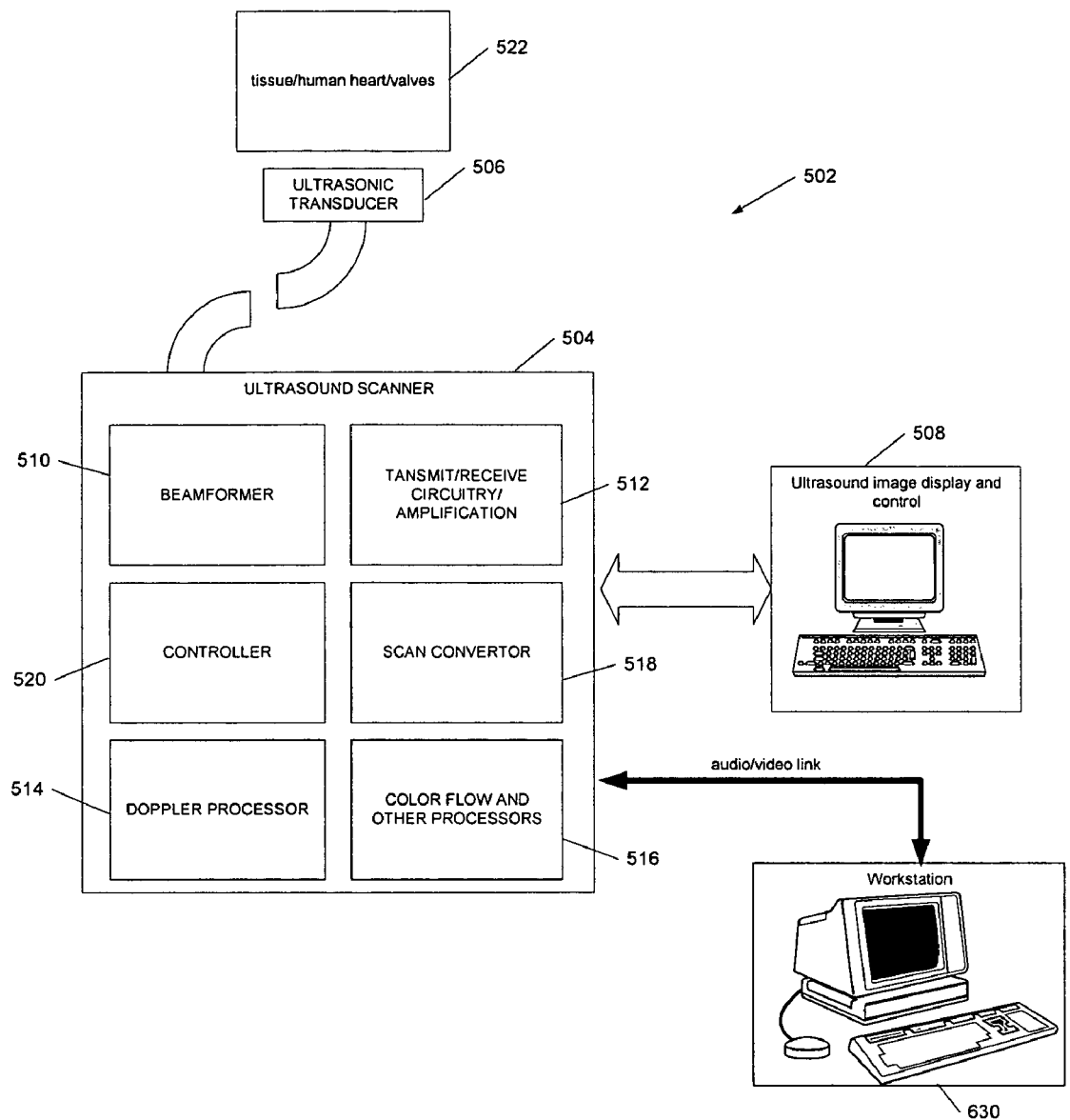
FIG. 7 is a block diagram of another embodiment of a Doppler scanner system.

FIG. 7 is a block diagram of another embodiment of a Doppler scanner system. In the embodiment illustrated in FIG. 7 the workstation 630 communicates only with the ultrasound scanner 504.

Figure 8:
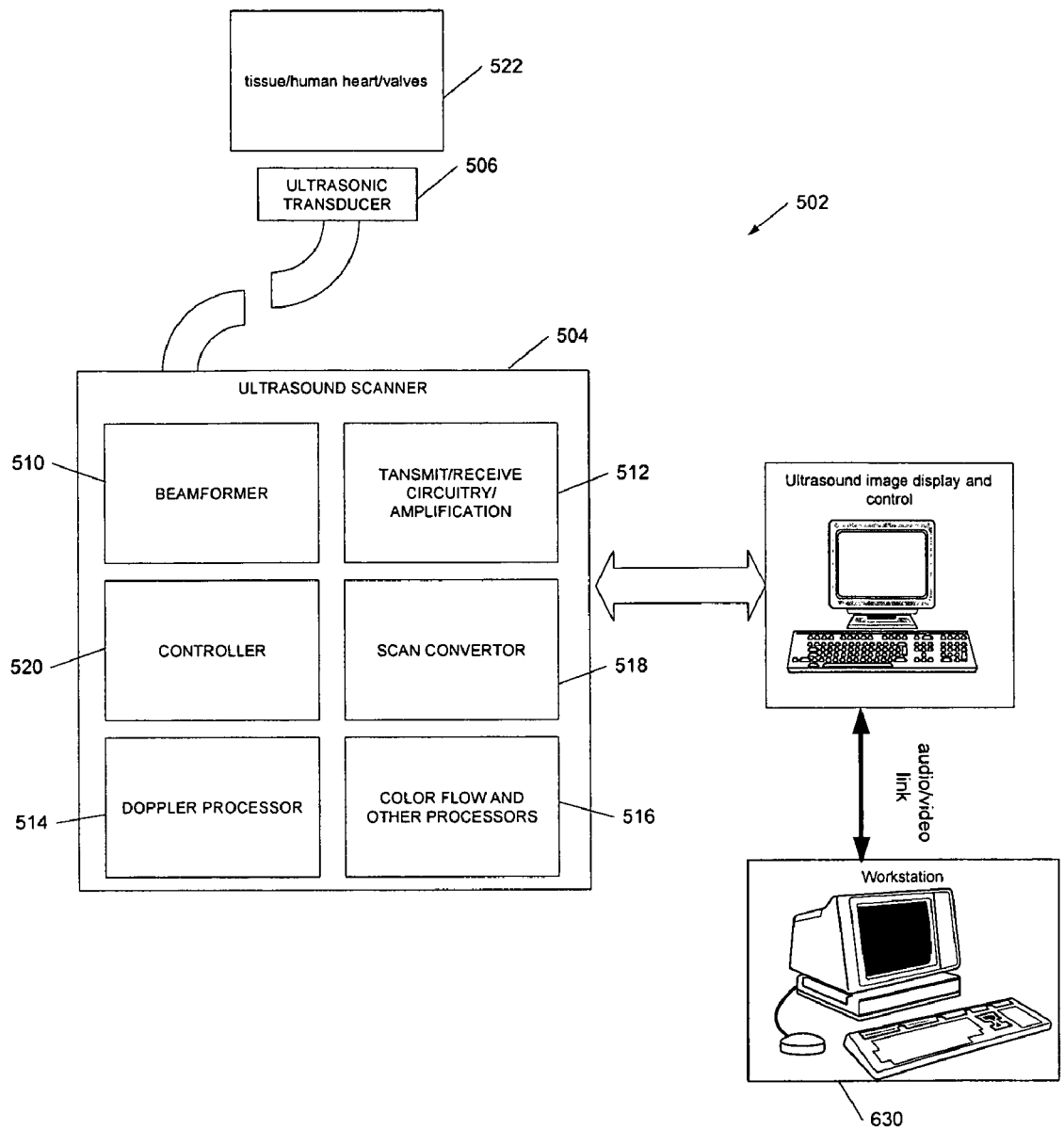
FIG. 8 is a block diagram of yet another embodiment of a Doppler scanner system.

FIG. 8 is a block diagram of yet another embodiment of a Doppler scanner system. In the embodiment illustrated in FIG. 8, the workstation 630 communicates only with the display 508.

Figure 9:
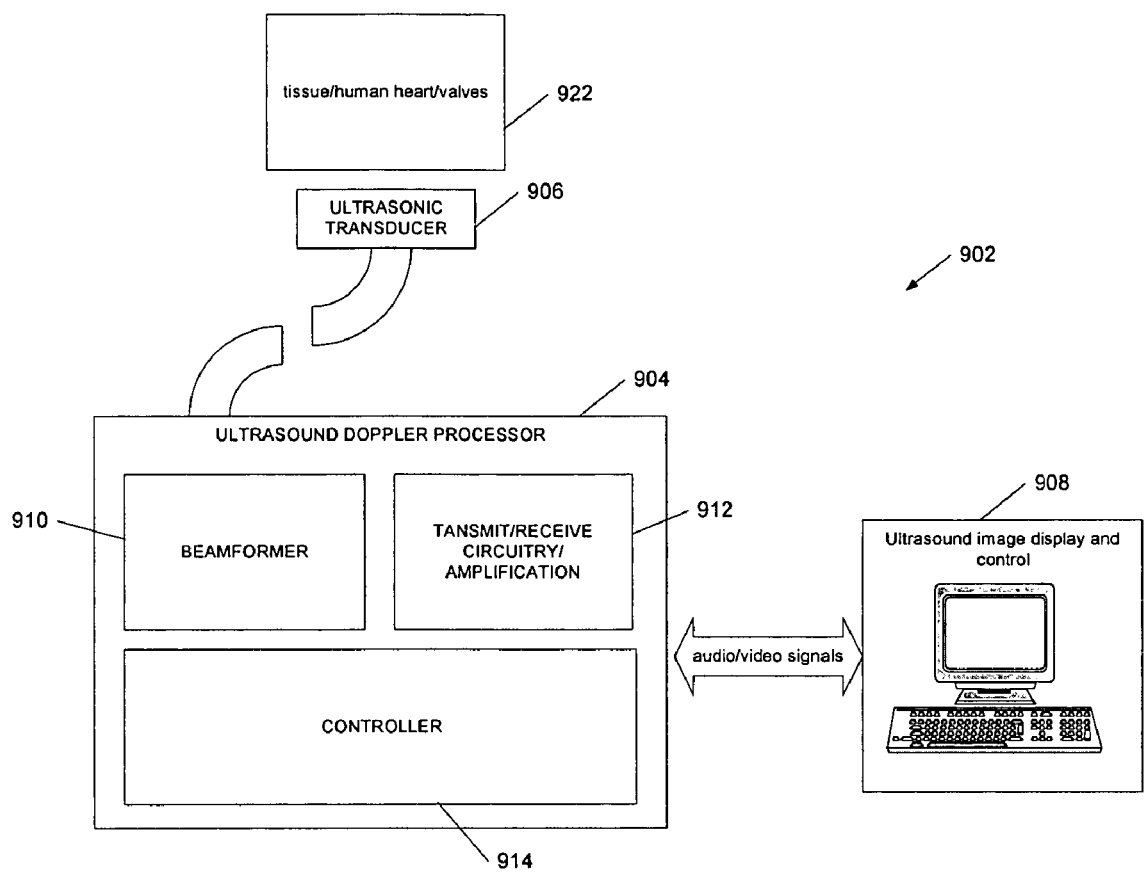
FIG. 9 is a block diagram illustrating another embodiment of a Doppler scanner system.

The previous embodiments describe a general Doppler scanner system. A system could also be implemented using a simple ultrasound Doppler processing set up. FIG. 9 is a block diagram illustrating another embodiment of a Doppler scanner system 902 constructed in accordance with the present invention. The system 902 includes an ultrasound Doppler processor 904, an ultrasonic transducer 906, and a display and control 908. The ultrasound Doppler processor 904 can be capable of intercepting and interpreting Doppler signals. The ultrasound Doppler processor 904 may include various circuits and subsystems for performing various functions. For example, the ultrasound Doppler processor 906 can include beamformer 910, transmit/receive 912 circuits or subsystems, and a controller 914. The ultrasound Doppler processor 904 may generate signals that are communicated to the ultrasonic transducer 906. The ultrasonic transducer transmits and receives signals from a desired sample 922, for example from a human heart tissue and blood. Signals received by the ultrasonic transducer 906 are communicated to the ultrasound Doppler processor 904. In one embodiment, the ultrasound Doppler processor 904 processes the received signals, including color mapping, and the processed signal is communicated to the display 908 for presentation to a user. In another embodiment, the ultrasound Doppler processor 904 does some processing of the received signal and the display 908 includes a process that does some processing of the signal, for example color mapping, before presentation to a user. The amount of regurgitation may be determined in the ultrasound Doppler processor 904, or in a processor in the display 908, or both. In addition, determination of regurgitation may be determined in a separate workstation, not shown.

Other combinations of hardware and software may be used to perform the techniques described so as to achieve the operationally described. For example, there are multiple ways of interlinking the components that form this invention.

Figure 10:
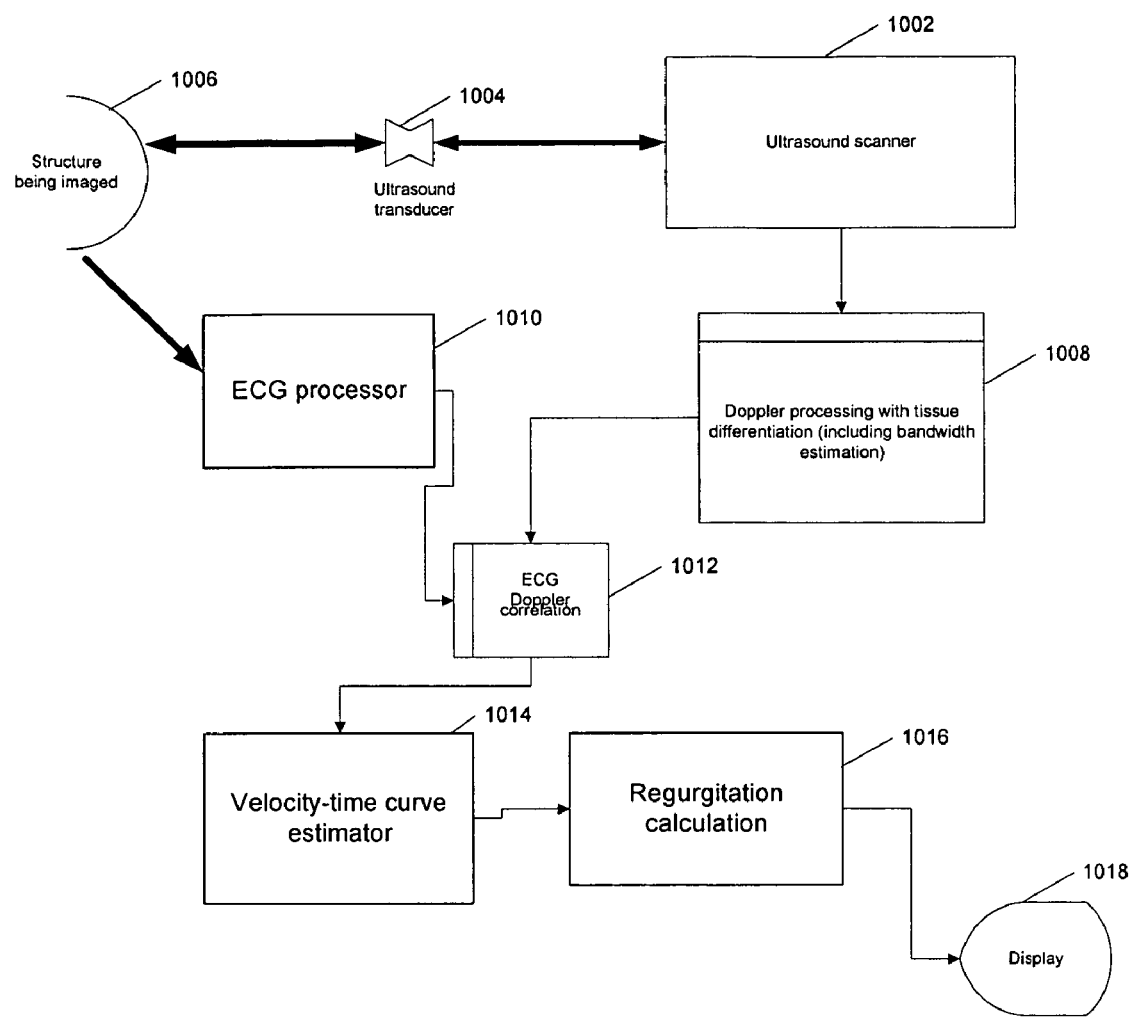
FIG. 10 is a process flow diagram illustrating a system for determining regurgitation.

FIG. 10 is a process flow diagram illustrating a system for determining regurgitation. An ultrasound scanner 1002 and an ultrasound transducer 1004 obtain ultrasound information from a structure 1006 being imaged, such as a heart value. The ultrasound scanner 1002 communicates the ultrasound information to a Doppler processor 1008. The Doppler processor 1008 processes the ultrasound information to differentiate signals received from tissue from those received from blood, and to determine the respective velocities. The Doppler processor may determine velocities using Doppler bandwidth estimation techniques.

Figure 11:
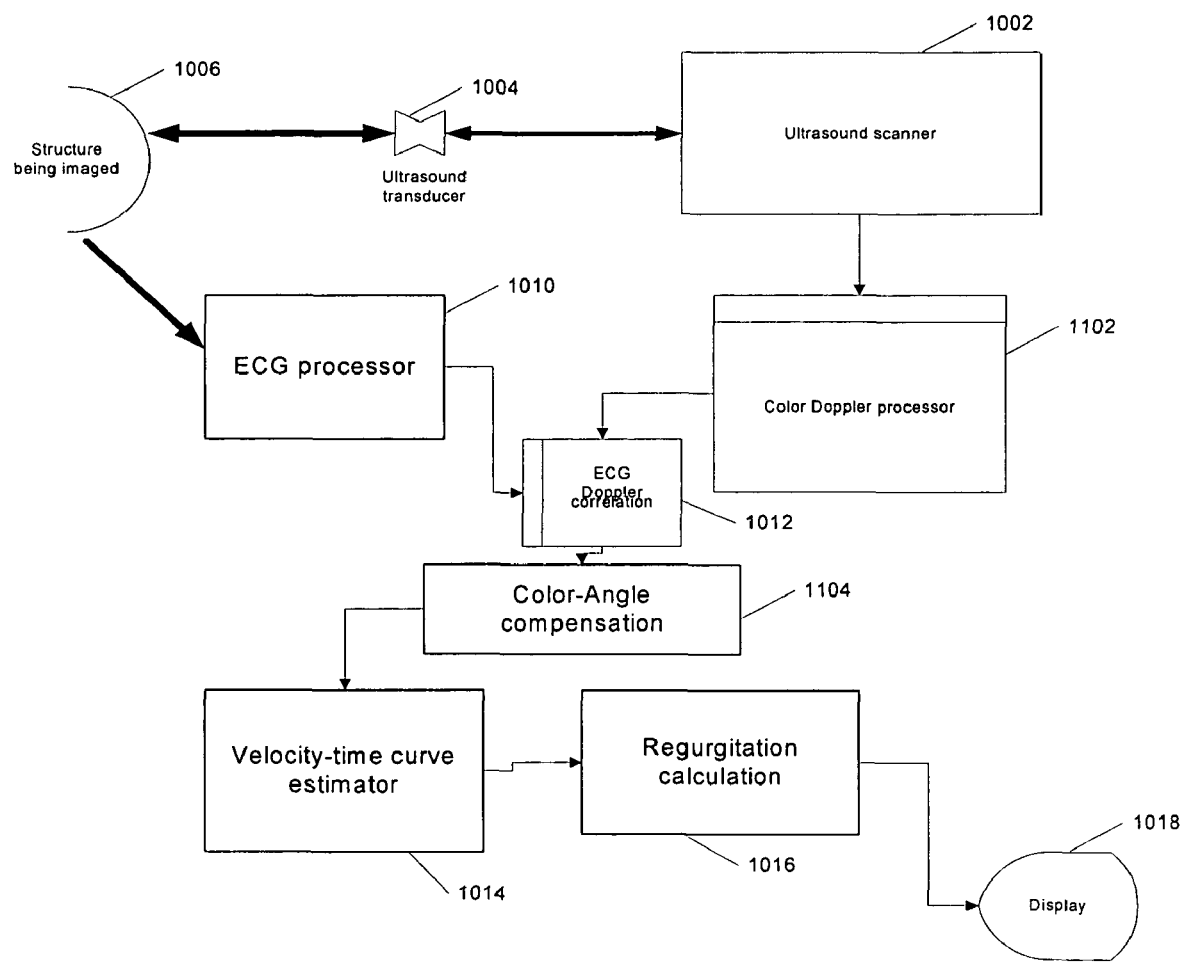
FIG. 11 is a process flow diagram illustrating another embodiment of a system for determining regurgitation.

Signals from the structure being imaged are also acquired by an ECG processor 1010. The output of the ECG processor and the Doppler processor 1008 are communicated to an ECG Doppler correlator 1012. The ECG Doppler correlator 1012 correlates the ECG and Doppler information, for example, to determine systole and diastole of the heart. The correlated information is communicated to a velocity-time curve estimator 1014 where estimates of the velocity, speed and direction, versus time are produced. The velocity-time curve estimates are then used in the regurgitation calculation engine 1016. The ECG information, Doppler information, velocity-time curves, and regurgitation calculations may then be presented to a user on a display 1018. It is noted that any combination of the ECG information, Doppler information, velocity-time curves, and regurgitation calculations may be displayed FIG. 11 is a process flow diagram illustrating another embodiment of a system for determining regurgitation. The exemplary system of FIG. 11 includes an ultrasound scanner 1002, ultrasound transducer 1004, structure being imaged 1006, ECG processor 1010, ECG Doppler correlator 1012, velocity-time curve estimator 1014, regurgitation calculation engine 1016, and display that operate in a manner similar to that described in connection with the system illustrated in FIG. 10.

The system illustrated in FIG. 11 also includes a color Doppler processor 1102 and a color-angle compensation engine 1104. The color Doppler processor 1102 receives ultrasound information from the ultrasound scanner 1002 and processes the information. Part of the processing by the color Doppler processor includes color coding the Doppler data to indicate speed and direction of flow in accordance with the color used to represent the data. The processed Doppler data is communicated to the ECG Doppler correlator 1012. The color-angle compensation engine 1102 receives correlated ECG and Doppler information from the ECG Doppler correlator 1012 and adjusts the color and magnitude of the Doppler data to compensate for the angle between the beam of the ultrasound beam and the direction of the blood flow. For example, the angle between the beam of the ultrasound beam and the direction of the blood flow may cause the measured Doppler shift, and corresponding velocity calculation, to be less than the actual Doppler shift that would occur if the angle between the beam and the direction of flow were zero, so that the beam and direction of flow are directly in-line with each other. The color-angle compensation engine 1104 adjusts the correlated ECG Doppler data magnitude, and corresponding color, to account for the errors due to the angle between the beam and direction of flow. The adjusted ECG Doppler data is communicated to the velocity-time curve estimator 1014.

Figure 12:
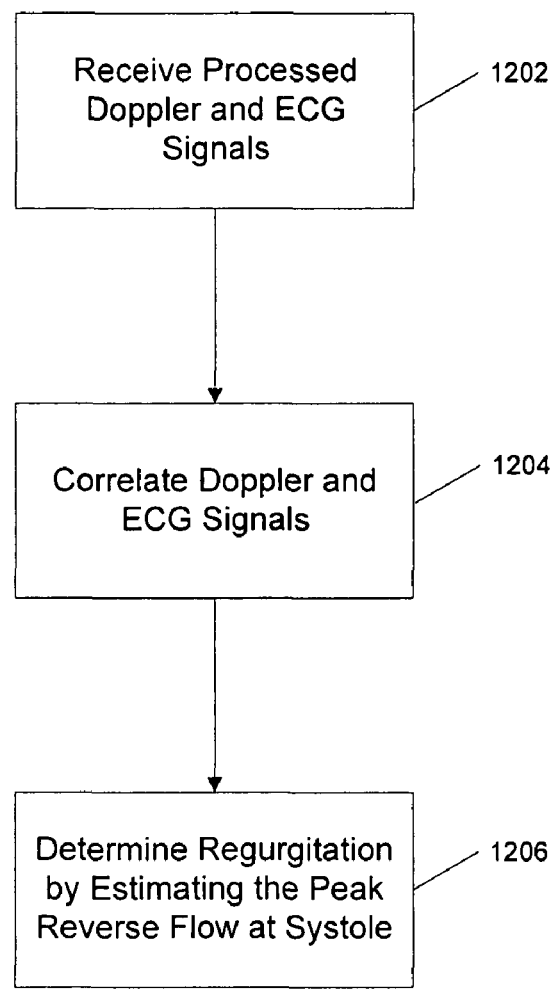
FIG. 12 is a flow diagram illustrating a method of determining regurgitation.

FIG. 12 is a flow diagram illustrating a method of determining regurgitation. The method begins in block 1202 where processed Doppler data and ECG signals are received. The processed Doppler signals include Doppler data that has been processed to distinguish the power, of amplitude of the spectrum, of the Doppler signal. Color has been assigned in accordance with the Doppler signals received from different types of material and corresponding different signal strengths. For example, different colors can be assigned to Doppler signals received from portions of the heart value versus Doppler signals received from blood. Flow continues to Block 1204.

In block 1204 the processed Doppler signals and ECG signals are correlated. Correlating the signals can be used, for example, to judge, or determine, the systole and diastole of a heart. Flow then continues to block 1206 where regurgitation is determined by estimating the peak reverse flow through the heart at systole.

Figure 13:
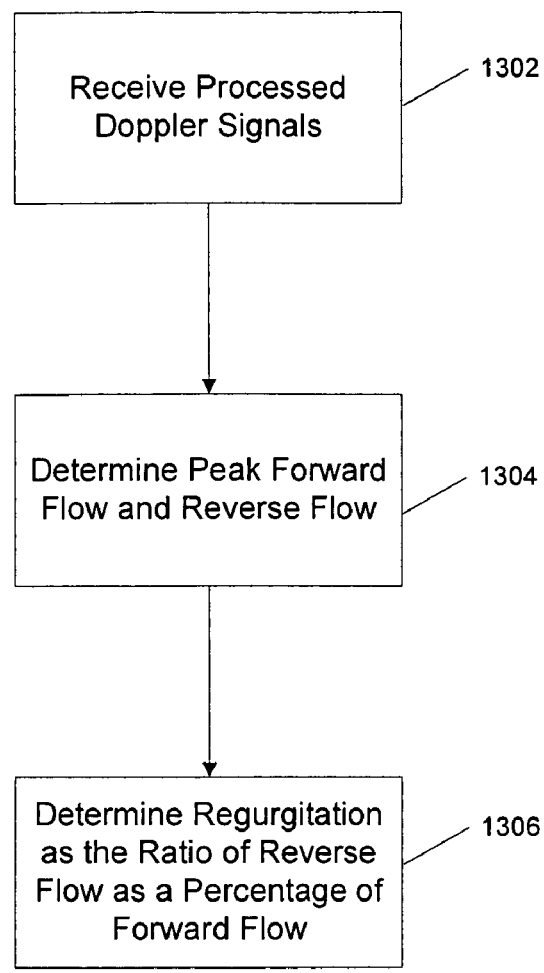
FIG. 13 is a flow diagram illustrating another method of determining regurgitation.

FIG. 13 is a flow diagram illustrating another method of determining regurgitation. Flow begins in block 1302 where processed Doppler signals are received. The processed Doppler signals include Doppler data that has been processed to distinguish the power, of amplitude of the spectrum, of the Doppler signal and had color assigned in accordance with the Doppler signals received from different types of material. For example, different colors can be assigned to Doppler signals received from portions of the heart value versus Doppler signals received from blood. Flow continues to block 1304.

In block 1304 the processed Doppler signals are examined to determine the peak forward and reverse flows during a given cardiac cycle. The cardiac cycle may be determined in numerous ways. For example, the cardiac cycle may be determined by the periodic repetition of a peak value, or a pattern of flow, or a positive to negative transition in a given direction. Flow then continues to block 1306 where regurgitation is determined as the ratio of the reverse flow as a percentage of the forward flow. The forward and reverse flows can be determined in various ways. For example the forward and reverse flows can be estimated by determining the area under the respective forward and reverse flow curves of the Doppler signals. It is beneficial to normalize, or correct, the flow curves according to the angle between the ultrasound beam and the direction of the blood flow.

Each step in the above flow, of determining the phases of the cardiac cycle, of detecting the peak flow velocities, and of judging the angle, can be performed automatically through appropriate processing on a computer, or can be manually performed by the user through the use of one or more user interface techniques, such as demarcating the point on a screen using a mouse or mouse button combination etc.

Those of skill in the art will understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill in the art will further appreciate that the various illustrative modules, circuits, and algorithms described may be implemented as electronic hardware, computer software, or combinations of both. Also, the various modules and circuits described may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, any conventional processor, controller, or micro controller. A processor may also be implemented as a combination of computing devices, e.g., a combination of a DSP and a microprocessor, a plurality of microprocessors, one or more microprocessors in conjunction with a DSP core, or any other such configuration. Software modules may reside in RAM memory, flash memory, ROM memory, EPROM memory, EEPROM memory, registers, hard disk, a removable disk, a CD-ROM, or any other form of storage medium known in the art.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method of determining heart valve regurgitation, the method comprising:
   transmitting ultrasonic signals towards a moving heart valve;
   receiving ultrasonic signals reflected from the moving heart valve and blood flowing through the heart valve;
   processing the received ultrasonic signals to obtain Doppler signals;
   processing received Doppler signals in accordance with received signal strength to differentiate between Doppler signals received from tissue of the moving heart valve from Doppler signals received from the blood flowing through the heart valve, and assigning color based upon signal strength to the Doppler signals from both the tissue of the moving heart valve and the blood flowing through the heart valve;
   processing the Doppler signals with assigned color from both the tissue of the moving heart valve and the blood flowing through the heart valve to obtain a velocity-time profile of the Doppler signals with different assigned colors for both the moving heart valve and the blood flowing through the heart valve; and
   determining heart valve regurgitation by estimating a peak reverse blood flow based upon the velocity-time profile of the Doppler signals with assigned color from the blood flowing through the heart valve at systole.

2. A method as defined in claim 1, wherein processing the Doppler data further comprises adjusting the Doppler data to compensate for an angle between an ultrasound beam and a direction of the blood flow.

3. A method as defined in claim 1, wherein the velocity-time profile of the processed Doppler signals are displayed to a user as a plot of velocity or Doppler shift of the blood flowing through the heart valve and the moving heart valve over time.

4. A method as defined in claim 1, further comprising receiving an ECG signal and correlating the ECG and Doppler signals so as to determine systole and diastole periods.

5. A method as defined in claim 4, wherein the ECG signals are displayed to a user together with the velocity-time profile of the processed Doppler signals displayed as a plot of velocity or Doppler shift of the blood flowing through the heart valve and the moving heart valve over time.

6. A method as defined in claim 1, wherein the processing and determining are performed in real-time.

7. A method as defined in claim 1, wherein the processing and determining are performed offline.

8. A method as defined in claim 1, wherein the Doppler signals are range gated.

9. A method as defined in claim 1, wherein processing the Doppler signals further comprises determining a bandwidth of the Doppler signal.

10. A method as defined in claim 1, wherein the Doppler signals are obtained from intra-cardiac examinations.

11. The method of claim 1, further comprising using a lookup table for assigning color based upon signal strength to the Doppler signals.

12. A method of determining heart valve regurgitation, the method comprising:
   transmitting ultrasonic signals towards a moving heart valve;
   receiving ultrasonic signals reflected from the moving heart valve and blood flowing through the heart valve;
   processing the received ultrasonic signals to obtain Doppler signals;
   processing the Doppler signals in accordance with a strength of a Doppler signal to differentiate between Doppler signals received from tissue of the moving heart valve from Doppler signals received from the blood flowing through the heart valve, and assigning color based upon signal strength to the Doppler signals from both the tissue of the moving heart valve and the blood flowing through the heart valve;

representing velocity or Doppler shift on a first axis and time on a second axis for the processed Doppler signals with assigned color from both the tissue of the moving heart valve and the blood flowing through the heart valve so as to represent the processed Doppler signals on a set of curves with different assigned colors representing the moving heart valve and the blood flowing through the heart valve;

examining the processed Doppler signals so as to determine a cardiac cycle; and determining heart valve regurgitation as a ratio of a reverse blood flow as a percentage of a forward blood flow, wherein the reverse blood flow and the forward blood flow are represented by an area under reverse flow and forward flow portions of the curve with assigned color representing the blood flowing through the heart valve.

13. A method as defined in claim 12, wherein processing the Doppler data further comprises adjusting the Doppler data to compensate for an angle between an ultrasound beam and a direction of the blood flow.

14. A method as defined in claim 12, wherein the set of curves with different assigned colors representing the moving heart valve and the blood flowing through the heart valve are displayed to a user as a plot of velocity or Doppler shift of the blood flowing through the heart valve and the moving heart valve over time.

15. A method as defined in claim 12, wherein the processing and determining are performed real-time.

16. A method as defined in claim 12, wherein the processing and determining are performed offline.

17. A method as defined in claim 12, wherein determining the cardiac cycle further comprises identifying a periodic repetition of a peak value in the processed Doppler data.

18. A method as defined in claim 12, wherein determining the cardiac cycle further comprises identifying a pattern of flow in the processed Doppler data.

19. A method as defined in claim 12, wherein determining the cardiac cycle further comprises identifying a positive to negative transition in the processed Doppler data.

20. A method as defined in claim 12, wherein the Doppler signals are range gated.

21. A method as defined in claim 12, wherein processing the Doppler data further comprises determining a bandwidth of the Doppler signal.

22. A method as defined in claim 12, wherein the Doppler signals are obtained from intra-cardiac examinations.

23. An apparatus for determining heart valve regurgitation, the apparatus comprising:

means for transmitting ultrasonic signals towards a moving heart valve;

means for receiving ultrasonic signals reflected from the moving heart valve and blood flowing through the heart valve;

means for processing the received ultrasonic signals to obtain Doppler signals;

means for processing the Doppler signals in accordance with a strength of a Doppler signal to differentiate between Doppler signals received from tissue of the moving heart valve from Doppler signals received from the blood flowing through the heart valve, and assigning color based upon signal strength to the Doppler signals from both the tissue of the moving heart valve and the blood flowing through the heart valve;

means for receiving an ECG signal;

means for correlating the ECG and Doppler signals so as to determine systole and diastole periods;

means for processing the Doppler signals with assigned color from both the tissue of the moving heart valve and the blood flowing through the heart valve to obtain a velocity-time profile of the Doppler signals with different assigned colors from both the moving heart valve and the blood flowing through the heart valve; and means for determining heart valve regurgitation by estimating a peak reverse blood flow based upon the velocity-time profile of the Doppler signals with assigned color from the blood flowing through the heart valve at systole.

24. An apparatus for determining heart valve regurgitation, the apparatus comprising:

means for transmitting ultrasonic signals towards a moving heart valve;

means for receiving ultrasonic signals reflected from the moving heart valve and blood flowing through the heart valve;

means for processing the received ultrasonic signals to obtain Doppler signals;

means for processing the Doppler signals in accordance with a strength of a Doppler signal to differentiate between Doppler signals received from tissue of the moving heart valve from Doppler signals received from the blood flowing through the heart valve, and assigning color based upon signal strength to the Doppler signals from both the tissue of the moving heart valve and the blood flowing through the heart valve;

means for representing velocity or Doppler shift on a first axis and time on a second axis for the processed Doppler signals with assigned color from both the tissue of the moving heart valve and the blood flowing through the heart valve so as to represent the processed Doppler signals on a set of curves with different assigned colors representing the moving heart valve and the blood flowing through the heart valve;

means for examining the processed Doppler signals so as to determine a cardiac cycle; and means for determining heart valve regurgitation as a ratio of a reverse blood flow as a percentage of a forward blood flow, wherein the reverse blood flow and the forward blood flow are represented by an area under reverse flow and forward flow portions of the curve with an assigned color representing the blood flowing through the heart valve.

25. The apparatus of claim 24, wherein the means for processing the Doppler signals in accordance with a strength of a Doppler signal comprises a lookup table for assigning color based upon signal strength to the Doppler signals.

26. An ultrasound system comprising:

an ultrasonic transducer configured to transmit and receive ultrasonic signals from a sample volume comprising blood flow through a moving heart valve; and an ultrasound scanner configured to communicate signals to the ultrasonic transducer to be transmitted into the sample, wherein the ultrasound scanner:

receives signals from the ultrasonic transducer that were reflected from blood and heart valve tissue, processes the received signals based on Doppler effect to determine velocity of the blood and heart valve tissue reflecting the signals and assigns color based upon signal strength to the received signals from both the tissue of the moving heart valve and the blood flowing through the heart valve to distinguish between the blood and heart valve tissue, processes the Doppler signals with assigned color from both the tissue of the moving heart valve and the blood flowing through the heart valve to obtain a velocity-time profile of the Doppler signals with different assigned colors for both the moving heart valve and the blood flowing through the heart valve, and determines heart valve regurgitation by estimating a peak reverse blood flow based upon the velocity-time profile of the Doppler signals with assigned color from the blood flowing through the heart valve at systole.

27. An ultrasound system as defined in claim 26, wherein determination of heart valve regurgitation is performed in a separate processor.

28. An ultrasound system as defined in claim 26, wherein systole is determined through correlation of the Doppler data to an ECG signal.

29. An ultrasound system as defined in claim 26, wherein processing the Doppler data further comprises adjusting the Doppler data to compensate for an angle between an ultrasound beam and a direction of the blood flow.

30. An ultrasound system as defined in claim 26, wherein the processed Doppler signals are displayed to a user as a plot of velocity or Doppler shift of the blood and heart valve over time.

31. An ultrasound system as defined in claim 26, wherein an ECG signal is displayed to a user.

32. An ultrasound system as defined in claim 26, wherein the processing and determining are performed real-time.

33. An ultrasound system as defined in claim 26, wherein the processing and determining are performed offline.

34. An ultrasound system as defined in claim 26, wherein the Doppler signals are range gated.

35. An ultrasound system as defined in claim 26, wherein processing the Doppler data further comprises determining a bandwidth of the Doppler signal.

36. An ultrasound system as defined in claim 26, wherein the ultrasonic transducer is included in a catheter.

37. An ultrasound system as defined in claim 36, wherein the catheter is used in intra-cardiac examinations.

38. An ultrasound system as defined in claim 26, wherein determining regurgitation comprises determining a ratio of reverse flow as a percentage of forward flow through a heart valve during a cardiac cycle.

39. An ultrasound system as defined in claim 38, wherein the reverse flow is determined by estimating an area of the Doppler data representing reverse flow.

40. An ultrasound system as defined in claim 38, wherein the forward flow is determined by estimating an area of the Doppler data representing forward flow.

41. An ultrasound system as defined in claim 38, wherein the cardiac cycle is determined from a periodic repetition of a peak value in the Doppler data.

42. A non-transitory computer readable media embodying instructions for performing a method of encoding data, the method comprising:

processing Doppler signals in accordance with a strength of a Doppler signal to differentiate between Doppler signals received from tissue of a moving heart valve from Doppler signals received from blood flowing through the heart valve, and assigning color based upon signal strength to the Doppler signals from both the tissue of the moving heart valve and the blood flowing through the heart valve;

correlating the ECG and Doppler signals so as to determine systole and diastole periods;

processing the Doppler signals with assigned color from both the tissue of the moving heart valve and the blood flowing through the heart valve to obtain a velocity-time profile of the Doppler signals with different assigned colors for both the moving heart valve and the blood flowing through the heart valve; and determining heart valve regurgitation by estimating a peak reverse blood flow based upon the velocity-time profile of the Doppler signals with assigned color from the blood flowing through the heart valve at systole.

43. A non-transitory computer readable media embodying instructions for performing a method of encoding data, the method comprising:

processing Doppler signals from a sample volume comprising blood flow through a moving heart valve in accordance with a strength of a Doppler signal to differentiate between Doppler signals received from tissue of the moving heart valve from Doppler signals received from the blood flowing through the heart valve, and assigning color based upon signal strength to the Doppler signals from both the tissue of the moving heart valve and the blood flowing through the heart valve;

representing velocity or Doppler shift on a first axis and time on a second axis for the processed Doppler signals with assigned color from both the tissue of the moving heart valve and the blood flowing through the heart valve so as to represent the processed Doppler signals on a set of curves with different assigned colors representing the moving heart valve and the blood flowing through the heart valve;

examining the processed Doppler signals so as to determine a cardiac cycle; and determining heart valve regurgitation as a ratio of a reverse blood flow as a percentage of a forward blood flow, wherein the reverse blood flow and the forward blood flow are represented by an area under reverse flow and forward flow portions of the curve assigned color representing the blood flowing through the heart valve.

* * * * *